US006375938B1

(12) United States Patent
Clothier, Jr. et al.

(10) Patent No.: US 6,375,938 B1
(45) Date of Patent: Apr. 23, 2002

(54) ANTIPERSPIRANT AND DEODORANT COMPOSITIONS CONTAINING A LOW MOLECULAR WEIGHT POLYETHYLENE GELLANT

(75) Inventors: James G. Clothier, Jr., Boston; Jeffrey R. Carlson, Sr., Pembroke; Dennis J. Colwell, Mansfield, all of MA (US)

(73) Assignee: The Gillette Company, Boston, MA (US)

( * ) Notice: Subject to any disclaimer, the term of this patent is extended or adjusted under 35 U.S.C. 154(b) by 0 days.

(21) Appl. No.: 09/842,560

(22) Filed: Apr. 26, 2001

(51) Int. Cl.[7] .............................. A61K 7/32; A61K 7/34; A61K 7/38; A61K 7/00; A61K 31/74
(52) U.S. Cl. .............................. 424/65; 424/66; 424/68; 424/78.02; 424/78.08; 424/400; 424/401
(58) Field of Search .............................. 424/65, 66, 68, 424/78.02, 78.08, 400, 401

(56) References Cited

U.S. PATENT DOCUMENTS

| 5,102,656 A | 4/1992 | Kasat ............................ 424/66 |
| 5,122,519 A | 6/1992 | Ritter ............................ 514/152 |
| 5,384,117 A | 1/1995 | Vu et al. ......................... 424/66 |
| 5,648,066 A | 7/1997 | Stepniewski .................. 424/64 |
| 6,103,250 A | 8/2000 | Brieva et al. ................. 424/401 |
| 6,139,824 A | 10/2000 | Ribery et al. .................. 424/65 |
| 6,177,066 B1 | 1/2001 | Pataut et al. .................. 424/65 |

FOREIGN PATENT DOCUMENTS

JP        61-69711        4/1986

*Primary Examiner*—Shelley A. Dodson
(74) *Attorney, Agent, or Firm*—Stephan P. Williams

(57) ABSTRACT

The present invention embraces an anhydrous topical antiperspirant or deodorant composition comprising an antiperspirant or deodorant active, a dermatologically acceptable volatile silicone liquid carrier vehicle and a polyethylene homopolymer dissolved in the vehicle to serve as a thickening or solidifying agent, wherein the polyethylene homopolymer has a molecular weight of about 200 to about 800 daltons, preferably about 300 to about 600 daltons, most preferably about 400 to about 500 daltons. The composition should be substantially free of any other organic or natural waxes. The present invention also embraces a method of inhibiting or reducing perspiration or a method of inhibiting or reducing malodor by topically applying an effective amount of such an antiperspirant composition or deodorant composition to the skin.

24 Claims, No Drawings

ANTIPERSPIRANT AND DEODORANT COMPOSITIONS CONTAINING A LOW MOLECULAR WEIGHT POLYETHYLENE GELLANT

BACKGROUND OF THE INVENTION

The present invention relates to anhydrous antiperspirant compositions and deodorant compositions that contain a low molecular weight polyethylene gellant. It also relates to a method of reducing perspiration or to a method of reducing malodor by topically applying an effective amount of such an antiperspirant composition or deodorant composition to the skin.

Antiperspirant and deodorant compositions are generally available in the form of liquid (for roll-on, porous dome or aerosol application), solid stick and soft solid or cream or gel. One type of known composition comprises a liquid carrier vehicle, such as a silicone or a polyhydric alcohol, an antiperspirant or deodorant active such as an aluminum or aluminum-zirconium antiperspirant salt or triclosan, and one or more gelling agents. Typical gelling agents include waxes such as paraffin and hydrogenated triglycerides (e.g. castor wax), fatty alcohols such as stearyl alcohol, fatty amides such as stearamide MEA, 12-hydroxystearic acid (including esters and amides thereof), N-acyl amino acid amides, and dibenzylidene sorbitol. U.S. Pat. Nos. 5,102,656 and 5,384,117 mention polyethylene homopolymer as one of several possible types of gelling agents for certain antiperspirant compositions, but neither of these patents exemplifies any actual antiperspirant formulations containing polyethylene homopolymer. Moreover, the polyethylene homopolymers generally available at that time have molecular weights in excess of 1500 daltons, have poor solubility in volatile silicone and make poor gellants in the absence of co-solvents.

U.S. Pat. No. 6,139,824 discloses deodorant compositions which are water-in-oil emulsions. The description suggests that the fatty (or oil) phase can include one or more waxes and mentions polyethylene wax in a list of possible waxes. Example 1 provides a deodorant stick that includes water (44.95%), cyclomethicone (22.50%), and Polywax 500 polyethylene (12.5%). U.S. Pat. No. 6,177,066 discloses solid deodorant and antiperspirant compositions that are essentially anhydrous and that include, as a solidifying agent, a mixture of waxes containing at least one polyethylene wax and at least one natural wax, both of which have a melting point greater than 80° C.

There has been an ongoing effort to improve the application aesthetics of antiperspirant and deodorant compositions, as well as the efficacy of such compositions. Currently the most efficacious antiperspirant compositions contain the so-called "enhanced efficacy" aluminum or aluminum-zirconium antiperspirant salts suspended in an anhydrous carrier. The enhanced efficacy aluminum and aluminum-zirconium antiperspirant salts include those described, for example, in GB 2,048,229 and U.S. Pat. No. 4,775,528 (high peak 4:3 ratio) and in U.S. Ser. No. 09/696,271 (Al peak 5>33%).

It would be highly desirable to provide an antiperspirant or deodorant composition that has improved application aesthetics such as a smooth, tack-free application without feeling cold, wet or oily, without leaving a visible residue, and with improved glide as well as decreased drag and stickiness. It would also be highly desirable to provide an antiperspirant or deodorant composition that is more efficacious—that is, inhibits perspiration or inhibits malodor to a greater degree—than those compositions which are currently available. It would be further desirable to provide an antiperspirant or deodorant composition that can be formulated with fewer ingredients than those compositions currently available because this would reduce costs, simplify manufacturing, and avoid ingredients that reduce efficacy.

It has now been discovered that superior antiperspirant and deodorant compositions can be made by including a low molecular weight polyethylene homopolymer as a thickening or solidifying agent.

SUMMARY OF THE INVENTION

The present invention embraces an anhydrous topical antiperspirant or deodorant composition comprising an antiperspirant or deodorant active, a dermatologically acceptable volatile silicone liquid carrier vehicle and a polyethylene homopolymer dissolved in the vehicle to serve as a thickening or solidifying agent, wherein the polyethylene homopolymer has a molecular weight of about 200 to about 800 daltons, preferably about 300 to about 600 daltons, most preferably about 400 to about 500 daltons. The composition should be substantially free of any other organic or natural waxes. The present invention also embraces a method of inhibiting or reducing perspiration or a method of inhibiting or reducing malodor by topically applying an effective amount of such an antiperspirant composition or deodorant composition to the skin.

DETAILED DESCRIPTION OF THE INVENTION

The present invention embraces an anhydrous topical antiperspirant or deodorant composition preferably comprising, by weight, about 0.01% to about 25%, more preferably about 0.1% to about 23%, antiperspirant or deodorant active, about 25% to about 98%, more preferably about 35% to about 95%, volatile silicone and about 1% to about 25%, more preferably about 2% to about 17%, polyethylene homopolymer dissolved in the volatile silicone. The polyethylene homopolymer has a molecular weight of about 200 to about 800 daltons, preferably about 300 to about 600 daltons, more preferably about 400 to about 500 daltons. Suitable polyethylene homopolymers include Performalene 400 (MW≡400) and Performalene PL (MW≡500) available from New Phase Technologies, Piscataway, N.J. By "anhydrous" is meant that the composition is substantially free (that is, contains less than 5%, preferably less than 2%, more preferably less than 1%, and most preferably less than 0.1% by weight) of free water (that is, excluding any water of hydration associated with the antiperspirant salt).

When the composition of the present invention is intended to be used as a topical deodorant, it will generally comprise, by weight, about 0.01% to about 10%, preferably about 0.1% to about 6%, deodorant active. When the composition of the present invention is intended to be used as a topical antiperspirant, it will generally comprise, by weight, about 6% to about 25%, preferably about 10% to about 23%, antiperspirant active.

A suitable deodorant active may be any agent that inhibits, suppresses, masks or neutralizes malodor. These may include (1) antimicrobial or bactericidal agents which kill the bacteria responsible for malodor production, (2) agents which inhibit or suppress or interfere with the bacterial enzymatic pathway that produces malodor, (3) agents which mask or absorb or neutralize malodor or (4) fragrances, encapsulated fragrances, or fragrance precursors which produce fragrances in the underarm. Examples of such deodorant actives include triclosan, triclocarban, usnic acid salts, zinc phenolsulfonate, β-chloro-D-alanine, D-cycloserine, aminooxyacetic acid, cyclodextrin, sodium bicarbonate, fragrances, etc. Aluminum and aluminum-zirconium antiperspirant salts also function as deodorant active agents, even when used as relatively low levels (e.g., 1–9% by weight).

A suitable antiperspirant active may be any agent that inhibits or reduces perspiration from the skin, particularly the axilla (underarm). Antiperspirant actives include the aluminum and aluminum-zirconium antiperspirant salts, particularly the enhanced efficacy antiperspirant salts. Preferred compositions of the present invention will comprise, by weight, about 3% to about 25%, more preferably about 10% to about 23%, of an aluminum or an aluminum-zirconium antiperspirant salt (except, when in aerosol form, it will comprise about 3% to about 15% aluminum antiperspirant salt).

Preferred aluminum salts are those having the general formula $Al_2(OH)_{6-a}X_a$ wherein X is Cl, Br, I or $NO_3$, and a is about 0.3 to about 5, preferably about 0.8 to about 2.5, more preferably about 1 to about 2 (such that the Al to X mole ratio is about 0.9:1 to about 2.1:1). These salts generally have some water of hydration associated with them, typically on the order of 1 to 6 moles per mole of salt. Most preferably, the aluminum salt is aluminum chlorohydrate (i.e. X is Cl in the above formula), especially 5/6 basic aluminum chlorohydrate where a is about 1, such that the aluminum to chlorine mole ratio is about 1.9:1 to 2.1:1. Aluminum chlorohydrate is referred to as "ACH" herein.

Preferred aluminum-zirconium salts are mixtures or complexes of the above-described aluminum salts with zirconium salts of the formula $ZrO(OH)_{2-pb}Y_b$ wherein Y is Cl, Br, I, $NO_3$, or $SO_4$, b is about 0.8 to 2, and p is the valence of Y. The zirconium salts also generally have some water of hydration associated with them, typically on the order of 1 to 7 moles per mole of salt. Preferably the zirconium salt is zirconyl hydroxychloride of the formula $Zr(OH)_{4-b}Cl_b$ where b is about 0.7 to about 4.0 (which is intended to include the structure sometimes written as $ZrO(OH)_{2-d}Cl_d$ where d is about 1 to 2). The aluminum-zirconium salts encompassed by the present invention have an Al:Zr mole ratio of about 2 to about 10, and a metal:X+Y ratio of about 0.73 to about 2.1, preferably about 0.9 to 1.5. A preferred salt is aluminum-zirconium chlorohydrate (i.e. X and Y are Cl), which has an Al:Zr ratio of about 2 to about 10 and a metal:Cl ratio of about 0.9 to about 2.1. Thus, the term aluminum-zirconium chlorohydrate is intended to include the tri-, tetra-, penta- and octachlorohydrate forms, with aluminum-zirconium tetrachlorohydrate being most preferred. Aluminum-zirconium chlorohydrate is referred to as "AZCH" herein. Generally, the aluminum-zirconium antiperspirant salts also contain a neutral amino acid such as glycine, typically in an amount to provide a Zr:Gly ratio of about 1:1 to about 1:4.

The preferred aluminum and aluminum-zirconium salts for use in compositions of the present invention are of the enhanced efficacy type. The enhanced efficacy salts are typically differentiated from conventional antiperspirant salts by reference to the various aluminum peaks that can be identified when the salt is analyzed by size exclusion chromatography, typically HPLC (high pressure liquid chromatography), of 10% aqueous salt solutions. A suitable chromatographic technique must be capable of resolving the Al into at least four distinct peaks (labeled peaks 2 (or 1+2), 3, 4 and 5, ), such as is shown in U.S. Pat. No. 5,330,751. One type of enhanced efficacy salt has been described as having an increased peak 4 content or an increased peak 4 to peak 3 ratio compared to conventional salts. (In some cases, enhanced salts have been described as having increased "band III" content by some authors, depending on the chromatographic technique and nomenclature employed. Generally, bands I, II, III and IV of one system correspond to peaks 1+2 (band I), 3, 4 and 5 of the other system.) Typically, the known enhanced efficacy salts (measured as 10% solutions) have an HPLC peak 4 to peak 3 area ratio of 0.5 or higher, preferably at least 0.7, with at least 70%, preferably at least 80%, of the aluminum contained in peaks 3 and 4. (The aluminum present in peaks 3 and 4 should be of the $Al^c$ type, not $Al^b$, when analyzed by the ferron test.) Thus, the enhanced salts will typically have a peak 4 content of at least 30% of the total aluminum contained in all the peaks (measured by peak area). In contrast, conventional non-enhanced antiperspirant salts have a negligible peak 4 content or a peak 4 to 3 area ratio less than 0.2, typically about 0.1.

A new type of enhanced efficacy aluminum-zirconium antiperspirant salt has been recently described in U.S. Ser. No. 09/696,271 in which at least 33%, preferably at least 45%, of the aluminum is found in HPLC peak 5. This salt may have greater efficacy than the aforementioned high peak 4 salts. Enhanced efficacy aluminum chlorohydrate is referred to as "EACH" herein. Enhanced efficacy aluminum-zirconium chlorohydrate with high peak 4 content is referred to as "EAZCH" herein. Enhanced efficacy aluminum-zirconium chlorohydrate with high peak 5 content is referred to as "$E^5AZCH$" herein.

Since the most effective antiperspirant salts currently in use are the enhanced efficacy aluminum-zirconium salts, the compositions of the present invention will preferably contain such salts, most preferably enhanced efficacy aluminum-zirconium chlorohydrate. Furthermore, such compositions should ideally contain the maximum amount of such salts that can be reasonably included within FDA guidelines without detracting from the application aesthetics of the final composition. Thus, the composition will ideally contain about 18% to about 25% by weight of the aluminum-zirconium salt (corresponds to about 15–20% active (USP)). However, since aerosol compositions are not currently permitted to contain zirconium, when the compositions of the present invention are formulated as an aerosol, they will preferably contain aluminum chlorohydrate, most preferably enhanced efficacy aluminum chlorohydrate. The amount of antiperspirant salt typically included in aerosol formulations is about 3% to about 15% by weight, preferably about 7% to about 12% by weight.

The compositions of the present invention may optionally include a water soluble calcium salt, such as calcium chloride. It has been recently suggested that the inclusion of a water soluble calcium salt may boost antiperspirant efficacy. The water soluble calcium salt may be included as part of the antiperspirant salt, as described in U.S. Pat. No. 6,042,816, or may be added separately to the formulation, as described in U.S. Pat. No. 5,955,065, where it will typically comprise about 1% to about 12% by weight.

The compositions of the present invention also include a dermatologically acceptable volatile silicone as the liquid carrier vehicle. Volatile silicones evaporate quickly and provide a dry feel. The volatile silicones include the cyclic polydimethylsiloxanes, also known as cyclomethicones, which have from about three to about seven, preferably about four to six, silicon atoms, and the linear polydimethylsiloxanes, also known as dimethicones, which have from about three to about eight, preferably about three to five, silicon atoms. The linear volatile silicones generally have viscosities of less than 5 cst, while the cyclic volatile silicones have viscosities under 10 cst. The composition may include a single volatile silicone or a mixture of volatile silicones. The composition may include, for example, about 25% to about 98%, preferably about 35% to about 95%, and more preferably about 40% to about 90%, volatile silicone by weight.

The volatile silicones generally have a significant vapor pressure at 25° C. The preferred volatile silicones are volatile methyl siloxanes, which are low viscosity silicones corresponding to the average unit formula $(CH_3)_a SiO_{(4-a)/2}$ in which a has an average value of two or three. The volatile methyl siloxanes may be linear or cyclic. Representative units are monofunctional "M" units $(CH_3)_3SiO_{1/2}$ and difunctional "D" units $(CH_3)_2SiO_{2/2}$. The presence of trifunctional "T" units $(CH_3)_2SiO_{2/3}$ results in the formation of branched cyclic volatile methyl siloxanes. The presence of tetrafunctional "Q" units $SiO_{2/4}$ results in the formation of branched linear volatile methyl siloxanes.

Volatile linear methyl siloxanes (volatile "dimethicones") have the formula $(CH_3)_3SiO\{(CH_3)_2SiO\}_x Si(CH_3)_3$, and volatile cyclic methyl siloxanes ("cyclomethicones") have the formula $\{(CH_3)_2SiO\}_y$. In the formulas x is 0–6, preferably 1–5, more preferably 1–3, and y is 3–10, preferably 4–6. Preferably the volatile methyl siloxane has a boiling point less than 250° C. and a viscosity of 0.65–10 centistokes ($mm^2$/s), preferably about 1–5 centistokes ($mm^2$/s). Branched methyl siloxanes include linear and cyclic methyl siloxanes in which one or more of the methyl groups have been replaced by $(CH_3)SiO$.

Examples of representative volatile linear methyl siloxanes include octamethyltrisiloxane (MDM) which has a boiling point of 152° C., a viscosity of 1.04 $mm^2$/s, and formula $Me_3SiO(Me_2SiO)SiMe_3$, decamethyltetrasiloxane ($MD_2M$), which has a boiling point of 194° C., a viscosity of 1.53 $mm^2$/s, and formula $Me_3SiO(Me_2SiO)_2SiMe_3$; dodecamethylpentasiloxane ($MD_3M$), which has a boiling point of 229° C., a viscosity of 2.06 $mm^2$/s, and formula $Me_3SiO(Me_2SiO)_3SiMe_3$; and tetradecamethylhexasiloxane ($MD_4M$), which has a boiling point of 245° C., a viscosity of 2.63 $mm^2$/s, and formula $Me_3SiO(Me_2SiO)_4SiMe_3$.

Examples of volatile cyclic methyl siloxanes include octamethylcyclotetrasiloxane ($D_4$), which has a boiling point of 176° C., a viscosity of 2.3 $mm^2$/s, and formula $\{(Me_2)SiO\}_4$; and decamethylcyclopentasiloxane ($D_5$), which has a boiling point of 210° C., a viscosity of 3.87 $mm^2$/s, and formula $\{(Me_2)SiO\}_5$; dodecamethylcyclohexasiloxane ($D_6$), which has a boiling point of 245° C., a viscosity of 6.62 $mm^2$/s, and formula $\{(Me_2)SiO\}_6$.

Examples of branched volatile methyl siloxanes include heptamethyl-3-{(trimethysilyl)oxy}trisiloxane ($M_3T$), which has a boiling point of 192° C., a viscosity of 1.57 $mm^2$/s, and formula $C_{10}H_{30}O_3Si_4$; hexamethyl-3,3,bis-{(trimethylsilyl)oxy}trisiloxane ($M_4Q$), which has a boiling point of 222° C., a viscosity of 2.6 $mm^2$/s, and formula $C_{12}H_{36}O_4Si_5$; and pentamethyl {(trimethylsilyl)oxy}cyclotrisiloxane ($MD_3$), which has a formula $C_8H_{24}O_4Si_4$.

One advantage of the composition of the present invention is that no other ingredients are necessary to achieve a highly desirable formulation beyond the three specified components, namely active, volatile silicone and polyethylene homopolymer gelling agent. This makes it possible to formulate simple, but effective compositions at reduced costs, with simplified manufacturing, and without ingredients that reduce efficacy. Thus, one embodiment of the present invention is a topical composition that consists essentially of an antiperspirant or deodorant active, a dermatologically acceptable volatile silicone, and a polyethylene homopolymer dissolved in the volatile silicone. Naturally, of course, one would normally include a fragrance in even a simple formula such as this, and possibly a colorant or preservative, but none of these are viewed as an ingredient that materially affects the basic and fundamental characteristics of the composition.

The composition of the present invention may also optionally include other ingredients typically found in cosmetic products. For example, it may optionally include a non-volatile emollient to improve emolliency and application aesthetics (e.g. reduced tackiness, slower dry-down, reduced drag and reduced whitening). The non-volatile emollient may be generally included in an amount of about 0% to about 25%, preferably about 2% to about 20%, more preferably about 5% to about 15%, by weight. Preferably the non-volatile emollient will be less than about one-half the amount of volatile silicone present in the composition, and more preferably will be less than about one-third the amount of volatile silicone. Generally, the amount of non-volatile emollient should be kept to a minimum so as not to adversely affect efficacy.

When present, the preferred non-volatile emollient is a non-volatile silicone. The non-volatile silicones typically have viscosities of about 5 to about 1000 cst, preferably about 10 to 500 cst, and include polyalkylsiloxanes such as dimethicone (e.g. DC 200) and polyalkylarylsiloxanes such as phenyltrimethicone (e.g. DC 556). Although less preferred, other types of liquid non-volatile emollients include paraffinic hydrocarbons such as mineral oil and hydrogenated polyisobutene, aliphatic alcohols such as octyldodecanol, fatty alcohol esters such as $C_{12-15}$ alcohols benzoate and myristyl octanoate, fatty acid esters such as isopropyl palmitate, myristyl myristate and octyl isononanoate, dicarboxylic acid esters such as diisopropyl sebacate, polyethylene glycols and polypropylene glycols such as PEG-40 and PPG-20, polyethylene and/or polypropylene glycol ethers of $C_{4-20}$ alcohols such as PPG-10 butanediol, PPG-14 butyl ether, PPG-5-Buteth-7, PPG-3-Myreth-3, and Steareth-20, and polyethylene and/or polypropylene glycol esters of $C_{4-20}$ acids such as PEG-8 Distearate and PEG-10 Dioleate.

The composition of the present invention may also optionally include a lower alkanol such as ethanol, a polyhydric alcohol such as propylene glycol or dipropylene glycol, suspending agents such as clays (e.g. quaternium-18 hectorite) and silicas, and fillers such as talc, polyolefins and modified corn starch. Although the composition may optionally include an additional non-wax thickening agent (e.g., hydroxypropyl cellulose), it should be substantially free (that is, contains less than 1%, preferably less than 0.1%), more preferably completely free, of any organic or natural waxes such as hydrogenated castor oil, ozokerite, stearyl alcohol, etc. However, it may optionally include a silicone wax. It is most preferred that the composition utilize polyethylene homopolymer as the sole gelling or thickening agent.

The foregoing list of materials is by way of example only and is not intended to be a comprehensive list of all potential materials that may be useful in an antiperspirant or deodorant composition. Obviously, the skilled worker may select those materials that provide the desired application and aesthetic characteristics of the particular form of composition to be produced.

The compositions of the present invention may be readily formulated as an aerosol, pump spray, liquid, roll-on, lotion, cream, gel, solid (both hard and soft), etc. When formulated as a liquid or lotion, the composition will typically include about 1% to about 3% polyethylene homopolymer. Liquid formulations may be used, for example, in roll-on and porous dome dispensers, as well as in pump spray dispensers and disposable wipes. When formulated as a cream, soft gel or soft solid, the composition will typically include about 4% to about 7% polyethylene homopolymer. When formulated as a solid, the composition will typically include about 8% to about 20% polyethylene homopolymer. Obviously, these amounts will vary somewhat depending upon the nature and amount of other ingredients in the formulation.

An aerosol may be easily produced by first making a liquid concentrate comprising the active, volatile silicone and polyethylene homopolymer, then adding propellant in an amount such that the final product comprises about 55% to about 85%, preferably about 60% to about 80% propellant. A preferred aerosol composition will comprise, in addition to the aforementioned propellant, about 3% to about 15% of an aluminum antiperspirant salt, about 0.2% to about 2% polyethylene homopolymer, and about 5% to about 35% volatile silicone. The propellant may include any of those currently available such as the volatile hydrocarbons (typically with 3 to 6 carbon atoms) and halohydrocarbons having a vapor pressure of 15 to 80 psig, preferably 30 to 70 psig, at about 20° C. These include propellant A-46, propellant A-31, propellant A-70, and propellant 152A.

The present invention also embraces a method of inhibiting or reducing perspiration by topically applying an effective amount of an antiperspirant composition as described herein to the skin of a human, preferably to the axilla, where such reduction in perspiration is desired by the user. An effective amount is that amount which provides at least a 20% sweat reduction, preferably at least a 40% sweat reduction, when tested in accordance with a standard hot room thermal efficacy protocol, and most preferably that amount which reduces perspiration to a degree that is noticeable by the user. Typically, the amount of antiperspirant composition applied will range from about 0.1 gram to about 1.0 gram per axilla depending on the formulation or such amount as will deliver about 0.01 to about 0.25 gram of antiperspirant active per axilla.

The present invention additionally embraces a method of inhibiting or reducing malodor by topically applying an effective amount of a deodorant composition as described herein to the skin of a human, preferably to the axilla, where such reduction in malodor is desired by the user. An effective amount is that amount which reduces malodor to a degree that is noticeable by the user. Typically, the amount of deodorant composition applied will range from about 0.1 gram to about 1.0 gram per axilla depending on the formulation or such amount as will deliver about 0.0001 to about 0.1 gram of deodorant active per axilla.

The present invention may be further illustrated by the following examples in which the parts and percentages are by weight. In each of these examples, the antiperspirant salts are of the enhanced efficacy type (EACH or EAZCH) and have an HPLC peak 4 to peak 3 area ratio greater than 0.7 with at least 80% of the aluminum contained in said peaks 3 and 4.

EXAMPLES 1 TO 4—LIQUID ANTIPERSPIRANT OR DEODORANT

Liquid antiperspirant or deodorant compositions are prepared having the ingredients and the amounts set out below. Each of these compositions is prepared by mixing all of the ingredients (except fragrance) to form a homogeneous suspension, heating to about 75°–90° C. to melt and dissolve the polyethylene homopolymer, and cooling the mixture with stirring, the fragrance being added while cooling.

|  | Weight Percent | | | |
| --- | --- | --- | --- | --- |
| Ingredient | Ex. 1 | Ex. 2 | Ex. 3 | Ex. 4 |
| Cyclomethicone (DC 245) | 78.8 | 77.8 | 78.3 | 97.2 |
| Al-Zr tetrachlorohydrate-gly | 20.0 | 20.0 | 20.0 | |
| Triclosan | | | | 0.3 |
| Polyethylene (MW ≅ 400) | 1.0 | 2.0 | | 2.0 |
| Polyethylene (MW ≅ 500) | | | 1.5 | |
| Fragrance | 0.2 | 0.2 | 0.2 | 0.5 |

EXAMPLES 5 TO 7—AEROSOL ANTIPERSPIRANT OR DEODORANT

Aerosol antiperspirant or deodorant compositions are prepared having the ingredients and the amounts set out below. Each of these compositions is prepared by mixing all of the ingredients, except the propellant and fragrance, to form a homogeneous suspension, heating to about 75°–90° C. to melt and dissolve the polyethylene homopolymer, and cooling the mixture with stirring, the fragrance being added while cooling, to form a liquid concentrate. The concentrate is then placed in an aerosol can and the propellant is added. The propellant is A-31, which is a mixture of isobutane, butane and propane having a vapor pressure of 31 psig.

|  | Weight Percent | | |
| --- | --- | --- | --- |
| Ingredient | Ex. 5 | Ex. 6 | Ex. 7 |
| Cyclomethicone (DC 344) | 14.0 | 14.0 | 20.0 |
| Aluminum chlorohydrate | 9.0 | 7.0 | |
| Polyethylene (MW ≅ 400) | 0.5 | 0.7 | 0.5 |
| Triclosan | | | 0.3 |
| Fragrance | | 0.2 | 0.8 |
| Propellant | 76.5 | 78.1 | 78.4 |

EXAMPLES 8 TO 12—SOLID STICK ANTIPERSPIRANT OR DEODORANT

Solid stick antiperspirant or deodorant compositions are prepared having the ingredients and the amounts set out below. Each of these compositions is prepared by mixing all of the ingredients (except the fragrance) to form a homogeneous suspension, heating to about 75°–90° C. to melt and dissolve the polyethylene homopolymer, and cooling the mixture to form a solid stick, with the fragrance being added during the cooling step and prior to solidification.

|  | Weight Percent | | | | |
| --- | --- | --- | --- | --- | --- |
| Ingredient | Ex. 8 | Ex. 9 | Ex. 10 | Ex. 11 | Ex. 12 |
| Cyclomethicone (DC 245) | 61.8 | 46.3 | 50.0 | 44.3 | 89.2 |
| Al-Zr tetrachlorohydrate-gly | 25.0 | 23.0 | 25.0 | 25.0 | |
| Triclosan | | | | | 0.3 |
| Dimethicone (50 cst.) | | 15.0 | | | |
| Dimethicone (350 cst.) | | | 15.0 | | |

-continued

| Ingredient | Weight Percent | | | | |
|---|---|---|---|---|---|
| | Ex. 8 | Ex. 9 | Ex. 10 | Ex. 11 | Ex. 12 |
| Octyldodecanol | | | | 15.0 | |
| Polyethylene (MW ≅ 400) | 12.5 | 15.0 | | 15.0 | 10.0 |
| Polyethylene (MW ≅ 500) | | | 10.0 | | |
| Fragrance | 0.7 | 0.7 | | 0.7 | 0.5 |

EXAMPLES 13 TO 17—CREAM ANTIPERSPIRANT OR DEODORANT

Cream or soft solid antiperspirant or deodorant compositions are prepared having the ingredients and the amounts set out below. Each of these compositions is prepared by mixing all of the ingredients (except the fragrance) to form a homogeneous suspension, heating to about 75°–90° C. to melt and dissolve the polyethylene homopolymer, and cooling the mixture to form a stiff cream or soft solid, with the fragrance being added during the cooling step.

| Ingredient | Weight Percent | | | | |
|---|---|---|---|---|---|
| | Ex. 13 | Ex. 14 | Ex. 15 | Ex. 16 | Ex. 17 |
| Cyclomethicone (DC 245) | 55.3 | 53.3 | 57.3 | 71.0 | 80.0 |
| Al-Zr tetrachlorohydrate-gly | 25.0 | 25.0 | 23.0 | 25.0 | |
| Triclosan | | | | | 0.3 |
| Dimethicone (50 cst.) | | | 15.0 | | 15.0 |
| Dimethicone (350 cst.) | 15.0 | | | | |
| Dimethicone (1000 cst.) | | 15.0 | | | |
| Polyethylene (MW ≅ 400) | 4.0 | 4.0 | 4.0 | 4.0 | 4.0 |
| Talc | | 2.0 | | | |
| Fragrance | 0.7 | 0.7 | 0.7 | | 0.7 |

What is claimed is:

1. An anhydrous topical antiperspirant or deodorant composition comprising an antiperspirant or deodorant active, a dermatologically acceptable volatile silicone, and a polyethylene homopolymer dissolved in the volatile silicone, wherein the polyethylene homopolymer has a molecular weight of about 200 to about 800 daltons, and wherein the composition is substantially free of organic or natural wax.

2. The composition of claim 1 comprising, by weight, about 0.01% to about 25% antiperspirant or deodorant active, about 25% to about 98% volatile silicone and about 1% to about 25% polyethylene homopolymer.

3. The composition of claim 1 wherein the polyethylene homopolymer has a molecular weight of about 300 to about 600 daltons.

4. The composition of claim 1 wherein the polyethylene homopolymer has a molecular weight of about 400 to about 500 daltons.

5. The composition of claim 2 comprising, by weight, about 3% to about 25% of an aluminum or an aluminum-zirconium antiperspirant salt.

6. The composition of claim 5 comprising about 35% to about 95% volatile silicone.

7. The composition of claim 5 comprising about 40% to about 90% volatile silicone.

8. The composition of claim 6 wherein the polyethylene homopolymer has a molecular weight of about 300 to about 600 daltons.

9. The composition of claim 2 comprising, by weight, about 0.01% to about 10% of a deodorant active.

10. The composition of claim 2 additionally comprising, by weight, about 0% to about 25% of a non-volatile emollient.

11. The composition of claim 10 wherein the non-volatile emollient is a non-volatile silicone.

12. The composition of claim 6 additionally comprising, by weight, about 5% to about 15% of a non-volatile emollient.

13. The composition of claim 12 wherein the non-volatile emollient is a non-volatile silicone.

14. The composition of claim 1 in the form of an aerosol composition comprising, by weight, about 55% to about 85% of a propellant and about 20% to about 40% of a liquid concentrate comprising an antiperspirant or deodorant active, a dermatologically acceptable volatile silicone, and a polyethylene homopolymer dissolved in the volatile silicone, wherein the polyethylene homopolymer has a molecular weight of about 200 to about 800 daltons.

15. The composition of claim 14 comprising, by weight, about 55% to about 85% of a propellant, about 3% to about 15% of an aluminum antiperspirant salt, about 5% to about 35% volatile silicone, and about 0.2% to about 2% polyethylene homopolymer dissolved in the volatile silicone.

16. The composition of claim 2 in the form of a liquid composition comprising about 1% to about 3% polyethylene homopolymer.

17. The composition of claim 2 in the form of a cream, gel or soft solid composition comprising about 4% to about 7% polyethylene homopolymer.

18. The composition of claim 2 in the form solid composition comprising about 8% to about 20% polyethylene homopolymer.

19. The composition of claim 1 additionally comprising a non-wax thickening agent.

20. The composition of claims 1, 5, 10 or 12 wherein the polyethylene homopolymer is the sole gelling agent.

21. The composition of claim 1 consisting essentially of the antiperspirant or deodorant active, the volatile silicone, and the polyethylene homopolymer.

22. The composition of claim 21 additionally comprising a non-volatile emollient.

23. A method of reducing malodor from human skin comprising topically applying to human skin a malodor reducing effective amount of an anhydrous deodorant composition comprising a deodorant active, a dermatologically acceptable volatile silicone, and a polyethylene homopolymer dissolved in the volatile silicone, wherein the polyethylene homopolymer has a molecular weight of about 200 to about 800 daltons, and wherein the composition is substantially free of organic or natural wax.

24. A method of reducing perspiration from human skin comprising topically applying to human skin a perspiration reducing effective amount of an anhydrous antiperspirant composition comprising an antiperspirant active, a dermatologically acceptable volatile silicone, and a polyethylene homopolymer dissolved in the volatile silicone, wherein the polyethylene homopolymer has a molecular weight of about 200 to about 800 daltons, and wherein the composition is substantially free of organic or natural wax.

* * * * *